(12) United States Patent
Winder et al.

(10) Patent No.: US 7,199,068 B2
(45) Date of Patent: *Apr. 3, 2007

(54) REACTIVE DISTILLATION ALKYLATION PROCESS INCLUDING IN SITU CATALYST REGENERATION

(75) Inventors: J. Barry Winder, Austin, TX (US); Donald L. Wharry, Austin, TX (US); John R. Schell, Austin, TX (US); Mary J. Brown, Cedar Park, TX (US); Joy L. Murray, Austin, TX (US); Richard C. Howe, Round Rock, TX (US); Wayne L. Sorensen, Austin, TX (US); Daniel P. Szura, Georgetown, TX (US); Frank Gates, Leander, TX (US)

(73) Assignee: Sasol North America Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/090,859

(22) Filed: Mar. 5, 2002

(65) Prior Publication Data

US 2003/0171204 A1 Sep. 11, 2003

(51) Int. Cl.
*B01J 20/34* (2006.01)

(52) U.S. Cl. ..................................... 502/31

(58) Field of Classification Search ............ 502/29–31; 585/447
See application file for complete search history.

(56) References Cited

U.S. PATENT DOCUMENTS

| 5,019,669 A | 5/1991 | Adams et al. ............... 585/446 |
|---|---|---|
| 5,082,990 A | 1/1992 | Hsieh et al. ................. 585/467 |
| 5,258,560 A | 11/1993 | Marker ........................ 568/697 |
| 5,326,923 A * | 7/1994 | Cooper et al. ............... 585/725 |
| 5,648,579 A * | 7/1997 | Kulprathipanja et al. ... 585/447 |
| 5,672,798 A * | 9/1997 | Zhang et al. ................ 585/467 |
| 5,712,213 A * | 1/1998 | Joly et al. ....................... 502/31 |
| 5,770,782 A | 6/1998 | Knifton et al. .............. 585/467 |
| 5,811,626 A * | 9/1998 | Joly et al. .................... 585/731 |
| 6,315,964 B1 | 11/2001 | Knifton et al. .............. 422/190 |

* cited by examiner

*Primary Examiner*—Edward M. Johnson
(74) *Attorney, Agent, or Firm*—C. James Bushman; Browning Bushman P.C.

(57) ABSTRACT

A unified process which couples a unique in situ catalyst regeneration process with a continuous reactive distillation under pressure for the alkylation of light aromatic hydrocarbons such as benzene with $C_2$–$C_{30}$ olefins using a solid acid alkylation catalyst supported in the reflux zone of a distillation column. Periodic regeneration of the catalyst is carried out with a countercurrent injection of a $C_4$–$C_{16}$ paraffin below the benzene rectification zone at the top of the column, but above the catalyst zone while the aromatic hydrocarbon reaction feedstock is injected continuously at a point above a rectification zone at the base of the column where the aromatic compound is separated from the paraffin and by-products washed from the catalyst. The use of the $C_4$–$C_{16}$ paraffin with the aromatic at a mole fraction in the range of 40 to 90% enables a regeneration temperature of about 175–250° C. to be achieved and maintained by adjusting the column pressure and aromatic reflux rate. Significantly lower pressures, on the order of 125 to 370 psig, are required to achieve regeneration temperature than would be otherwise required with the use only of the aromatic hydrocarbon to dilute and wash the by-products from the catalyst surfaces.

7 Claims, 6 Drawing Sheets

REACTIVE DISTILLATION ALKYLATION PROCESS INCLUDING IN SITU CATALYST REGENERATION

FIELD OF THE INVENTION

This invention relates to catalyst regeneration. More particularly, this invention relates to the in situ regeneration of solid acid catalysts in a unified, continuous, pressurized, reactive distillation process for the alkylation of light aromatic compounds, such as benzene and cumene.

BACKGROUND OF THE INVENTION

The alkylation of aromatic compounds with olefins is an established commercial technology. For example, benzene alkylated with short chain (typically 2 to about 6 carbons) hydrocarbons has value as gasoline octane enhancer. Light aromatic compounds alkylated with longer chain (that is, having greater than about 8–10 carbon atoms) linear olefins are commonly sulfonated to produce surfactants suitable for use in detergent manufacture.

The alkylation of benzene and other light aromatic compounds has typically been carried out using hydrofluoric acid or a solid acid catalyst in a fixed bed, plug flow process. For example, U.S. Pat. No. 2,860,173 discloses the use of a solid phosphoric acid as a catalyst for the alkylation of benzene with propylene to produce cumene. More recently, the use of Friedel Crafts catalysts, especially aluminum chloride and certain natural zeolites and synthetic commercial sieves, as alkylation catalysts, has been taught.

Still more recently, alkylation of benzene and light aromatics with $C_6$–$C_{30}$ olefin co-fed with the aromatic over a solid catalyst bed in a reactive distillation column has been proposed carried out in a reactive distillation column (U.S. Pat. No. 5,770,782).

However, there continue to be problems associated with commercial alkylation processes. For one thing, most of the above processes have practical limits on the amount of aromatic that can be economically co-fed with the olefins, thus resulting in low yields of the desired alkylated products. The typical range for benzene to olefin mole ratio using HF alkylation technology is 4/1 to 8/1. The fixed bed, plug flow solid acid technology referred to above is practiced using a benzene/olefin molar ratio of 15/1 to 30/1. The examples proposed for reactive distillation in U.S. Pat. No. 5,770,782 used a 5/1 to 20/1 benzene/olefin mole ratio for the co-fed mixture and indicate a need for mechanical mixing of the aromatic and olefin before they enter the catalyst bed to assure adequate conversion and alkylate yield.

In addition, all these processes have a significant tendency to produce polysubstituted, in particular, dialkylated aromatics. Solid acid alkylation catalysts tend to deactivate more rapidly in the presence of dialkylated aromatic products. Carbonaceous deposits and heavy organics build up on the catalyst surface, with resultant decrease in catalyst effectiveness and a need to shut the process down to regenerate the catalyst. Most of these problems are directly related to the exothermic nature of the reaction, which has a tendency to be severe and difficult to control. Regeneration is typically provided using benzene maintained in the liquid phase at a pressure of 500 plus psig and temperatures in excess of 250° C.

It is clear that a need exists for a method of alkylation of light aromatics with straight chain olefins that has high olefin conversion rates, a high selectivity for mono-substituted products, and prolonged catalyst effectiveness. Reducing the severity of operating conditions would improve the likelihood of achieving such results.

SUMMARY OF THE INVENTION

This invention provides a unified reactive distillation process and system useful in the preparation of monoalkylated aromatic compounds by the solid acid-catalyzed reaction of light aromatic compounds with low molecular weight, straight chain olefins, which allows for the periodic in situ regeneration of the catalyst, i.e., in the distillation column.

The aromatic alkylation process of the invention involves a reactive distillation process and comprises a continuous, pressurized process using a distillation column configuration and system including a reactive zone, a first rectification zone at the top of the distillation column for rectification and recovery of unreacted aromatic hydrocarbon feedstock, an intermediate reactive zone containing a solid acid alkylation catalyst, and a second rectification zone positioned below and in communication with the reactive zone, where unreacted aromatic hydrocarbon and olefin feedstock may be separated from the alkylation product and any by-products. Below the second rectification zone is a reboiler and means for withdrawing the alkylation product from the column. Suitably positioned injectors allow for the controlled introduction of aromatic hydrocarbon compound and olefin feedstock.

In the reactive distillation alkylation process at least a portion of a suitable olefin feedstock is introduced at a point between the intermediate catalyst zone and the upper rectification zone, and at least a portion of a suitable aromatic hydrocarbon feedstock is introduced at a point between the catalyst zone and a second, lower, rectification zone, and the aromatic hydrocarbon is refluxed upwardly through the catalyst zone to contact and react with the descending olefin feedstock in a counter-current, liquid phase reaction. In such preferred system, the conditions of the reaction require that the internal pressure in the reactive zone is maintained constant and above about 1 atmosphere, preferably between about 20 and about 200 psig, and the combination of olefin and aromatic hydrocarbon in the reboiler maintained at or near reflux such that the temperature in the reboiler stays below the thermal degradation temperature for the alkylated product, which is about 265° C., and the molar ratio of the aromatic hydrocarbon to the olefin in the liquid phase can be maintained between about 30/1 to about 100/1, preferably between about 40/1 to about 80/1.

Regeneration of the catalyst in reactive distillation alkylation process is required as a result of a build-up on the surface of the catalyst of reaction by-products that "poison" the catalyst, lessening its effectiveness and causing a loss of conversion. According to a preferred aspect of the present invention, periodic regeneration of the alkylation catalyst can be accomplished in the distillation column periodically by ceasing flow of the olefin feedstock and injecting an effective amount of a suitable paraffin into the column counter-current to the flow of the aromatic hydrocarbon feedstock and adjusting the internal column pressure and temperature in the catalyst zone to achieve the desired regeneration temperature which, as is well known in this art, is within the range of above about 175° C., generally from about 175° C. to about 250° C.

Typically, the preferred regeneration method of the invention will be to periodically inject the paraffin into the distillation column at a point below the first rectification zone and above the catalyst, whereby the paraffin intermixes with the refluxing aromatic hydrocarbon feedstock in counter-current flow through the catalyst zone and, in combination with the aromatic hydrocarbon, dilutes and dissolves the by-products and other material from the catalyst surface and transports it into the reboiler for recovery and disposal.

The use of a counter-current flow of paraffin and aromatic hydrocarbon in the column provides an unexpected reduction in the required operating pressure to achieve the desired regeneration temperature in the catalyst zone. The process permits regeneration at milder conditions, e.g., 175–250° C., than typically environmental in a fixed bed process. The temperature may be adjusted using both the internal pressure of the column and the reflux rate of the aromatic hydrocarbon. For example, at a column pressure of 125 to 370 psig, a composition of 40–90 mole % aromatic hydrocarbon with paraffin can be employed.

DETAILED DESCRIPTION OF PREFERRED EMBODIMENTS

Figure 1:
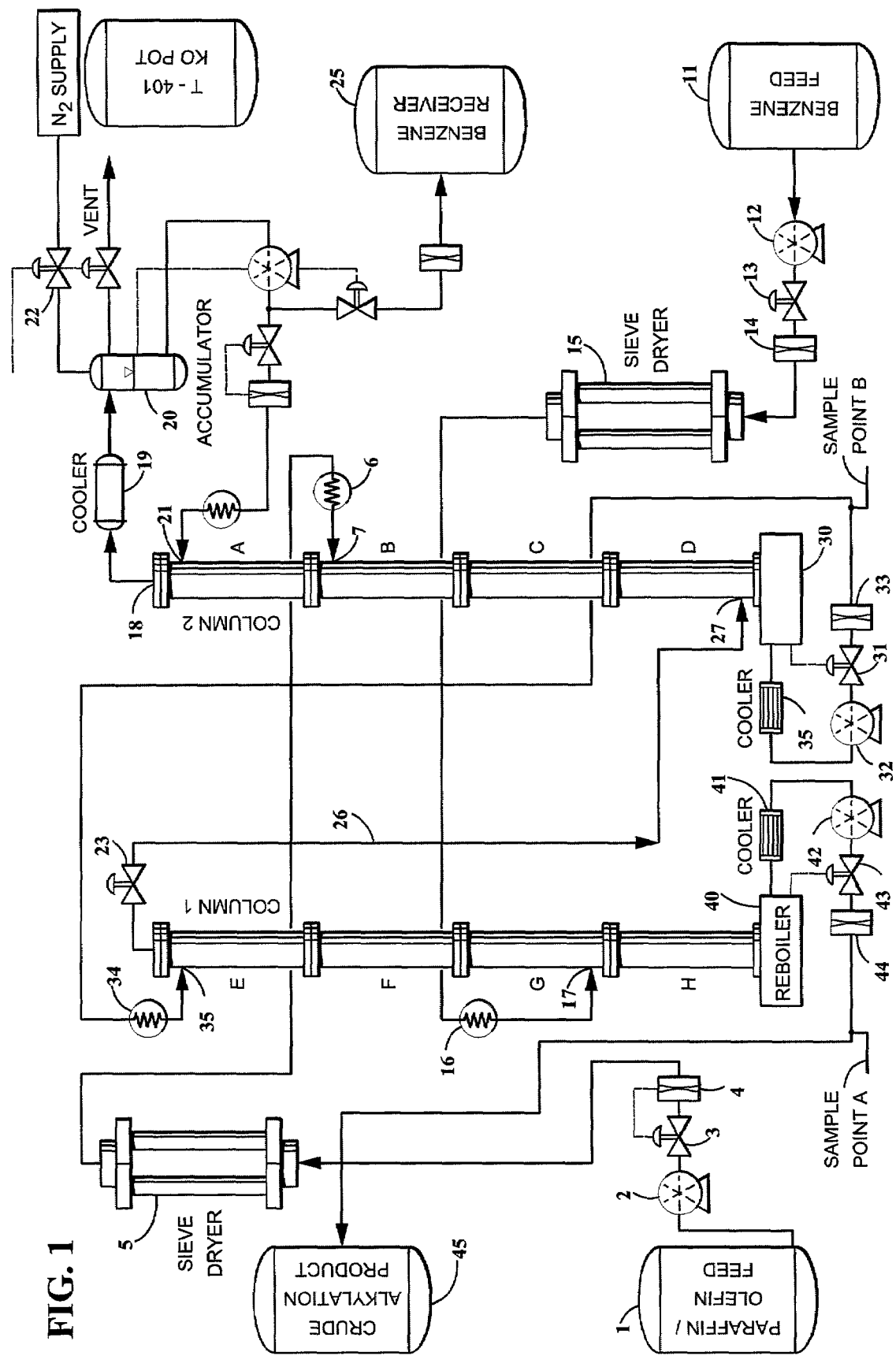
FIG. 1 provides a schematic representation of a continuous reactive distillation alkylation system using the catalyst regeneration process of the present invention. The depiction shows two separate and connected columns performing as a single system.

By light aromatics or aromatic, we mean organic aromatic compounds having one or more rings and from 6-to about 20 carbon atoms, that boil at or below about 250° C. under pressure conditions typical in a commercial reactor-type distillation column. The preferred members of this group are benzene, toluene, xylene, styrene, phenol and cumene, with benzene being especially preferred.

The preferred olefins include those straight chain mono-unsaturated olefins having from 2 to about 30 carbon atoms, preferably from about 8 to about 20 carbon atoms and, more preferably, from 10 to 14 carbon atoms. A particularly preferred olefin feedstock for detergent range alkylate comprises a mixture of $C_6$–$C_{18}$ olefins with $C_6$–$C_{18}$ paraffins derived from a commercial paraffin dehydrogenation process.

The preferred paraffins or paraffin feedstock suitable for use in the alkylation catalyst regeneration process of the present invention include paraffins having from $C_4$ to $C_{16}$ carbon atoms. In the case of gasoline range alkylation, paraffins of $C_4$ to $C_{16}$ carbon content, are preferred while in the case of detergent range alkylation, paraffins of $C_8$ to $C_{16}$ carbon content are preferred.

The catalyst regeneration process of the present invention is conveniently carried out in a unified, continuous reactive alkylation process such as that disclosed in co-pending U.S. application Ser. No. 10/091199, filed concurrently herewith and entitled "A Reactive Distillation Process for the Alkylation of Aromatic Hydrocarbons", the disclosure of which is hereby incorporated by reference. In that process, using a reactive distillation configuration such as that disclosed in accompanying FIG. 1, an olefin/paraffin mixture is injected below the benzene rectification zone at the top of the distillation column, but above the catalyst zone. The aromatic hydrocarbon is continuously injected at a point below the solid catalyst reactive zone and above a rectification zone, in which it can be separated from the alkylated product, paraffin and unreacted olefin that descends from the reactive zone on its way to the reboiler.

The alkylation reaction takes place primarily in the liquid phase on the solid catalyst in the reactive zone. Catalysts that may be employed for this invention include such acid zeolitic materials as W-Zeolite, beta-zeolite, acidic mordenite, acid clays, such as montmorillonite and medium pore zeolites such as ZSM-5, ZSM-12, ZSM-18, ZSM-20, MCM-22, and BETA, L, Y, mordenite, as well as rare earth exchanged forms or de-aluminated forms of the listed zeolites. Other catalysts that may be employed in the practice of this invention are the fluorided versions of the above-mentioned zeolites and aluminum chloride impregnated on alumina, clays and silica-alumina. The catalyst can be maintained in place by supporting it on structured packing, such as Koch-Glitch KATAMAX brand catalytic structured packing, or alternatively arranged in other ways familiar to those skilled in this art, for example, in a series of beds on perforated trays or in beds positioned in the liquid down comers of a trayed distillation column. The structured can also be used in the rectification zones, without catalyst, to improve the evaporation and condensation efficiency in those zones.

During the alkylation process, as disclosed in the referenced application, the molar ratio of the aromatic hydrocarbon to the liquid phase olefin in the reactive zone is maintained through adjustment of the column internal back pressure, the aromatic hydrocarbon reflux rate, the energy input into the reboiler, the amount of aromatic hydrocarbon removed while maintaining the column at or approaching total reflux, and the input flow of aromatic hydrocarbon. Coupling the reflux rate of the aromatic hydrocarbon with the relatively low introduction of additional aromatic hydrocarbon into the column will tend to increase the composition of aromatic hydrocarbon refluxing into the reactive zone and keep the molar ratio of the aromatic hydrocarbon to the olefin in the reactive catalyst zone at a higher level.

The higher mole ratios of aromatic hydrocarbon to olefin that can be generated with counter-current flow of the liquid phase olefin and the higher reflux of aromatic compound into the reactive zone has been demonstrated to have several unexpected advantages:

First, the higher aromatic compound to olefin mole ratios in the reactive zone enables a larger catalyst zone, tending to stabilize the reaction and make it very isothermal in the distillation column. Prior attempts to keep an isothermal process typically involved mixing the aromatic hydrocarbon with the feed of the olefin/paraffin mixture;

Second, higher energy input to the reboiler to produce the higher reflux rates will be without the risk of exceeding the thermal degradation temperature that can occur in the reboiler at temperatures exceeding 265° C. High aromatic hydrocarbon reflux rates at constant energy input will tend to decrease the reboiler temperature as they force more aromatic hydrocarbon into the reboiler. Raising the internal pressure within the column can achieve higher catalyst reaction temperatures, thereby increasing yield, without the risk of exceeding a thermal degradation temperature in the reboiler.

Third, the higher aromatic hydrocarbon to olefin molar ratios, as well as the isothermal nature of the reaction zone, can help increase the usable life of the catalyst. This is the result of the higher selectivity of the process of this invention for the mono-substituted alkylation, as opposed to poly-alkylation, which is known to poison most solid acid alkylation catalysts, requiring more frequent regeneration.

In the example set forth below, the regeneration process of this invention was carried out in a continuous reactive distillation column depicted in FIG. 1. As shown in FIG. 1, for convenience, two separate columns were employed and designed to perform as a single reactive distillation column. Differential pressure control established vapor transport between the lower half (column 1) and the upper half (column 2). Liquid transport between upper segments (column 2) and lower segments (column 1) was handled by a pump and flow control from the base of column 2.

The catalysts employed were solid acid mordenite and Y zeolites. The catalyst is granulated to a 16×40 U.S. mesh size, dried at an appropriate temperature to activate it, and loaded into 54 KATAMAX catalyst packing elements. Each element has a 2 inch outside diameter and is 5.5 inches long. The mass of catalyst loaded into the column will depend on its density. However, since each of the KATAMAX elements all had the same internal catalyst volume (50.8cc), the catalyst was equally distributed by using 9 KATAMAX elements in each of Sections B, C, D, E, F, and G as shown in FIG. 1. Transition from detergent range alkylation to catalyst regeneration is made by stopping the injection of the $C_{10}$–$C_{14}$ paraffin/olefin mixture and replacing it with a $C_8$–$C_{16}$ paraffin, while maintaining the benzene flow rate and reflux rate at the base of the column. In situ counter-current regeneration is achieved by raising the column pressure to between about 125 to 250 psig while maintaining the benzene flow at a relatively low rate with high reflux. Once the column pressure and benzene reflux become stable again, the paraffin is injected from the storage tank 1. The paraffin feed is pumped from a storage tank 1 at a controlled, rate using pump 2, Control Valve 3 and mass flow sensor 4.

The paraffin feed passes through a 4A molecular sieve bed 5 where it is dried, and then through preheater 6, where the temperature is adjusted to match the measured reflux temperature inside the column at the point of injection. The temperature is monitored and adjusted upward to match the reflux temperature as the paraffin composition in the column increases. The point of paraffin injection is conveniently the same point as the olefin feed, that is, just above the KATAMAX catalyst elements in Section B, which is just below Section A, the rectification zone that separates and refluxes the aromatic hydrocarbon (which, in each of the examples, is benzene). Benzene injection temperatures at the base of the column and at the benzene reflux injection point are adjusted upward to match the increase in the reflux temperature as the paraffin content increases. The regeneration in this counter-current manner is maintained for about 8 to about 36 hours, depending on such parameters as the type of catalyst being used and the degree to which it became deactivated.

Following regeneration, transition back to the alkylation mode is achieved by stopping the flow of paraffin while maintaining or adjusting the flow of the aromatic hydrocarbon at the base of the catalyst bed to maintain the aromatic hydrocarbon in reflux. The column temperature is allowed to cool back to alkylation reaction temperature, while in aromatic hydrocarbon reflux condition. This is accomplished generally by gradually decreasing the column pressure back to the pressure at which the alkylation reaction takes place. The refluxing of the aromatic hydrocarbon acts to cool the column relatively quickly.

At the appropriate temperature, olefin feedstock can be re-introduced to once again begin the alkylation process. In the example below, as in the referenced application, the preferred olefin feed set forth is a paraffin/olefin feedstock derived from a paraffin dehydrogenation process. The olefin/paraffin mixture is pumped from Feed Storage Tank 1 at a controlled rate, is passed through a 4A molecular sieve bed 5 where it is dried, and then through preheater 6, where the temperature is adjusted to match the measured reflux temperature inside the column at the point of injection. The injection temperature is monitored and adjusted upward to match the measured reflux temperature inside the distillation column at the point of injection. The point of olefin feed injection is just above the KATAMAX catalyst elements in Section B, which is just below Section A, the rectification zone that separates and refluxes the aromatic hydrocarbon (which, in each of the examples, is benzene).

The aromatic hydrocarbon is pumped from storage tank 11 using pump 12, with flow controlled by control valve 13 and monitored using mass flow meter 14. Prior to injection, the aromatic hydrocarbon is also passed through a molecular sieve dryer and is heated to about 5–10° C. below its boiling point at the experimental internal column pressure. Thus, it is injected as a liquid, but generally will quickly flash due to the heat from the liquid and vapor rising out of the reboiler. As depicted in FIG. 1, the injection point 17 of the aromatic hydrocarbon is at the base of Section G, but above the rectification zone (Section H) which is immediately above the reboiler 40. This is the primary injection point and sets up the counter-current flow of aromatic hydrocarbon with the olefin descending as a liquid from its injection point 7 (above the catalyst in Section B).

The aromatic hydrocarbon employed in the example was benzene. Benzene vapor in the column is taken overhead and condensed in cooler 19 and accumulated in vessel 20. The accumulated benzene is reinjected as reflux at point 21 in rectification zone A. As will be appreciated by those skilled in the art, this can be through level control from the accumulator vessel 20 or on flow control to the column along with a stream that removes excess benzene storage to tank 25 using the appropriate monitoring and flow controlling apparatus.

The desired operating pressure is adjusted and maintained using cascade control with appropriate nitrogen injection and venting into and out of the accumulator tank 20. The two column configuration depicted in the drawing was also used in the example. The two columns were operated as one by means of heaters and flow control valves. The benzene vapor, as it leaves Section E and flows between the columns, is maintained at the appropriate temperature and pressure by means of an electrically heated and controlled vapor transport line 26. Benzene vapor enters the base of Section D of the column at point 27 and continues through segments D, C and B. The flow between the columns is controlled at control valve 23 using a relatively low differential pressure, usually about 2 psig.

Unreacted olefin and paraffin, as well as crude alkylate product, any by-product and liquid phase benzene are accumulated in vessel 30, below Section D, cooled at 35, and pumped to the top of SectionE on level control. The liquid from pump 32 is reheated at 34 to precisely the reflux temperature of the column at the injection point 35. The liquid then continues to descend through the catalyst zone (Sections E, F and G into rectification zone H and reboiler 40. Crude linear alkyl benzene product, paraffin, higher molecular weight bottoms product and trace levels of unreacted olefin, if present, removed through reboiler 40 on level control and pumped to storage in tank 45.

There are two liquid phase sample points at which the data on the crude alkylate product, as set forth in tables 1 and 2 below, were collected. Sample point A is the final product after passing through all catalyst sections. Sample point B is an intermediate product representing 50% of the catalyst residence time. A third sample point, not shown, can be at the base of the benzene overhead accumulator 20. This can be used to measure benzene purity.

EXAMPLE 1

A unique feature of the reactive distillation unit of the present invention is the ability to regenerate the catalyst in situ at a set of regeneration conditions that are in general milder then those required to regenerate a plug flow fixed bed catalytic reactor. Typically the fixed bed process calls for the use of pure benzene to be maintained in the liquid phase at 500 psig and 250° C. regeneration temperature.

Figure 2:
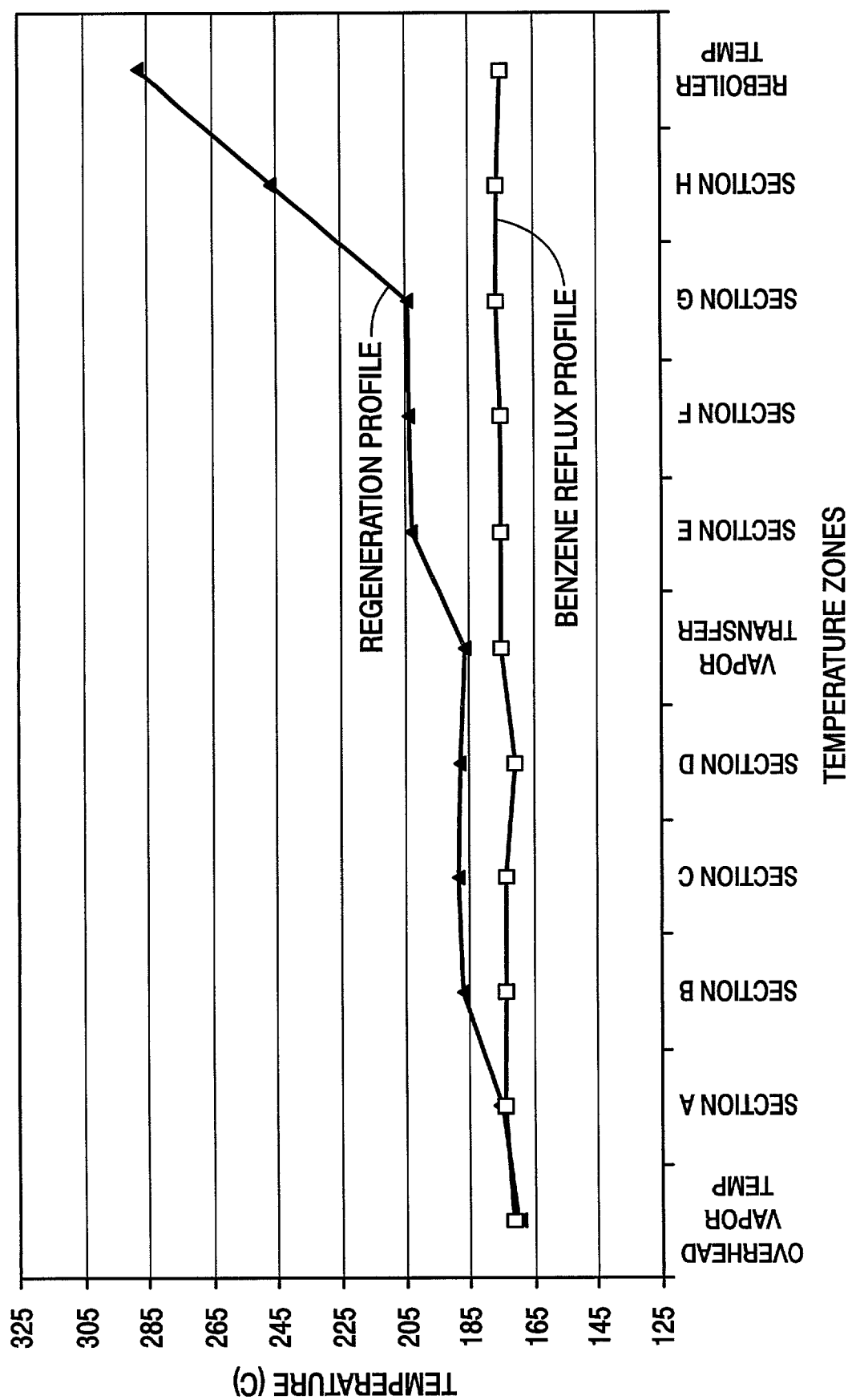
FIG. 2 is a graph showing the regeneration temperature profile throughout the column.

An example of catalyst deactivation and subsequent regeneration for the reactive distillation process was conducted as follows. A 1379.27 g of TOSOH 330Y was loaded into the 54 KATAMAX structured packing elements and placed in the reactive distillation column shown in FIG. 1. The reboiler was charged with benzene and the column was brought to reflux benzene at 50–52 psig column pressure. Paraffin/olefin feed shown in FIG. 1 as feed to section B was initiated at 50 g/min. Benzene injection at the base of the column, section G, was maintained at 10 g/min. The reactive distillation column was operated at the conditions listed in Table 2. Samples of liquid product were removed from two sample points. Sample point A is cooled liquid product removed from the reboiler and represents the total conversion in the reactive distillation column. Sample point B is a cooled liquid sample removed from the intermediate accumulator at the base of column, section D. This sample point represents the conversion at 50% of the catalyst volume. The TOSOH 330 Y zeolite solid acid catalyst was operated per the condition shown in Table 2 for a total of 118.5 hours on stream. During this operating period the TOSOH 330 Y experienced significant deactivation. The conversion at point B was initially 99.96% with a residual bromine index in the crude benzene, paraffin/olefin and alkylate product of 1.1 cg/g. The catalyst in sections B, C, and D experienced significant deactivation as the conversion dropped to 24.7% (Bromine Index 2185) at 118.5 hours on stream. Similarly Sections E, F, and G experienced deactivation from 100% conversion (Bromine Index non detectable) to 88.8% conversion with a residual bromine index of 829 cg/g. The catalyst deactivates from top to bottom in the distillation column. After 118.5 hours on stream, the paraffin/olefin mixture was discontinued and the column refluxed benzene at 134° C. for 2 hours as the crude alkylate is washed from the catalyst bed into the reboiler. During this period the paraffin/olefin feed in the storage tank was replaced with a paraffin feed of the same molecular weight and carbon number distribution as shown in Table 1. The column back pressure is increased to 125 psig and the benzene reflux stabilizes at 125 psig. A uniform column temperature of only 172–175° C. is achieved with benzene reflux at 125 psig back pressure. Paraffin injection is initiated at 50 g/min through H101 at a point just above the first section containing the catalyst structured packing. The counter-current paraffin injection alters the composition in the column which increases the reflux temperature. The counter-current paraffin flow establishes a regeneration temperature profile as shown in FIG. 2. This increases the column temperature profile from the uniform 172–175° C. with benzene reflux to the range of 187° to 205° C. Additional heating was applied to the column through skin heaters in order to reach the 200° C. regeneration temperature at 125 psig. The additional heating is required to achieve the regeneration temperature due to the mechanical upper pressure limit on the reactive distillation column. The regeneration conditions used in this example are paraffin rate: 50 g/min, benzene rate 10 g/min, column back pressure 125 psig, and benzene set on total reflux at the top of the column. This counter-current paraffin regeneration was maintained for 24 hours. The number of hours can vary from 8 to 36 hours depending on the degree of deactivation of the catalyst. Following regeneration, the paraffin flow is stopped, the column is cooled and pressure readjusted to 50 psig reaction pressure in a benzene reflux. Once the column is stable at 50 psig and under benzene reflux, the paraffin/olefin feed is re-established at the top of section G. The analysis of liquid samples from sample points A and B confirms that the catalyst has been completely regenerated.

TABLE 1

Capillary GC Analysis of Paraffin/Olefin Feed

| Feed | A Weight % | B Weight % |
|---|---|---|
| $<C_{10}$ | 0 | 0 |
| $C_{10}$ | 1.53 | 1.98 |
| $C_{11}$ | 3.85 | 3.71 |
| $C_{12}$ | 3.83 | 3.83 |
| $C_{13}$ | 2.45 | 2.44 |
| $C_{14}$ | 0.33 | 0.36 |
| $C_{15}$ | 0 | 0 |
| Total Olefin | 11.99 | 12.32 |
| Linear Paraffin | | |
| $<C_{10}$ | 0.18 | 0.07 |
| $C_{10}$ | 14.42 | 19.09 |
| $C_{11}$ | 31.84 | 29.72 |
| $C_{12}$ | 26.43 | 24.88 |
| $C_{13}$ | 14.42 | 13.25 |
| $C_{14}$ | 0.62 | 0.48 |
| $C_{15}$ | 0.19 | 0.2 |
| Total Paraffin | 88.1 | 87.69 |
| Avg MW (g/mole) | 163.6 | 162.9 |
| Bromine No. (Cg/g)) | 10.8 | 10.4 |

TABLE 2

| Time on Stream (hrs.) | Sample Point B Olefin % Conv | Sample Point B Bromine Index (cg/g) | Sample Point A Olefin % Conv | Sample Point A Bromine Index (cg/g) | Paraffin + Olefin Injection Rate (g/min) | Benzene Feed Injection Rate (g/min) | Column Pressure (psig) | Average Catalyst Zone Temp (° C.) | Reflux Benzene Injection Rate (g/min) | Liquid Phase Benzene/ Olefin Mole Ratio |
|---|---|---|---|---|---|---|---|---|---|---|
| 5 | 100 | 0 | 99.96 | 1.1 | 50.5 | 10.1 | 52 | 144 | 194 | 57 |
| 7 | 99.94 | 4.2 | 85.3 | 375 | 49.9 | 9.8 | 52 | 144 | 192 | 54 |
| 25 | 99.9 | 5 | 83.6 | 410 | 49.9 | 10.1 | 52 | 140 | 127 | 91 |
| 28 | 100 | 3 | 83.6 | 426 | 49.9 | 10.0 | 52 | 144 | 211 | 73 |
| 31 | 100 | 1 | 83.9 | 450 | 49.7 | 9.8 | 52 | 144 | 176 | 54 |
| 52 | 100 | 1 | 28.9 | 2347 | 49.7 | 10.0 | 51 | 144 | 163 | 46 |
| 54 | 100 | 1 | 28.3 | 2151 | 49.5 | 10.0 | 51 | 141 | 146 | 53 |
| 84.5 | 95.6 | 309 | 18.9 | 2351 | 49.8 | 9.8 | 51 | 143 | 167 | 55 |
| 88.5 | 95.6 | 293 | 20.6 | 2222 | 49.5 | 9.8 | 51 | 144 | 172 | 59 |
| 89.5 | 96.5 | 216 | 12.0 | 2199 | 50.1 | 10.1 | 52 | 144 | 171 | 58 |
| 116.5 | 84.5 | 1056 | 20 | 2080 | 50.1 | 10 | 52 | 144 | 177 | 62 |
| 118.5 | 88.8 | 829 | 24.7 | 2185 | 50.1 | 9.8 | 52 | 144 | 177 | 65 |
| Regeneration for 24 hours at 187–205° C. using Counter current Paraffin and Benzene ||||||||||| 
| 6 | 100 | 1 | 100 | 1 | 49.7 | 10 | 50 | 141 | 85 | 30 |
| 8 | 100 | 1 | 100 | 1 | 49.7 | 9.9 | 50 | 141 | 68 | 27 |
| 10 | 100 | 1 | 98.3 | 27 | 49.6 | 9.8 | 50 | 141 | 61 | 25 |

EXAMPLE 2

Figure 3:
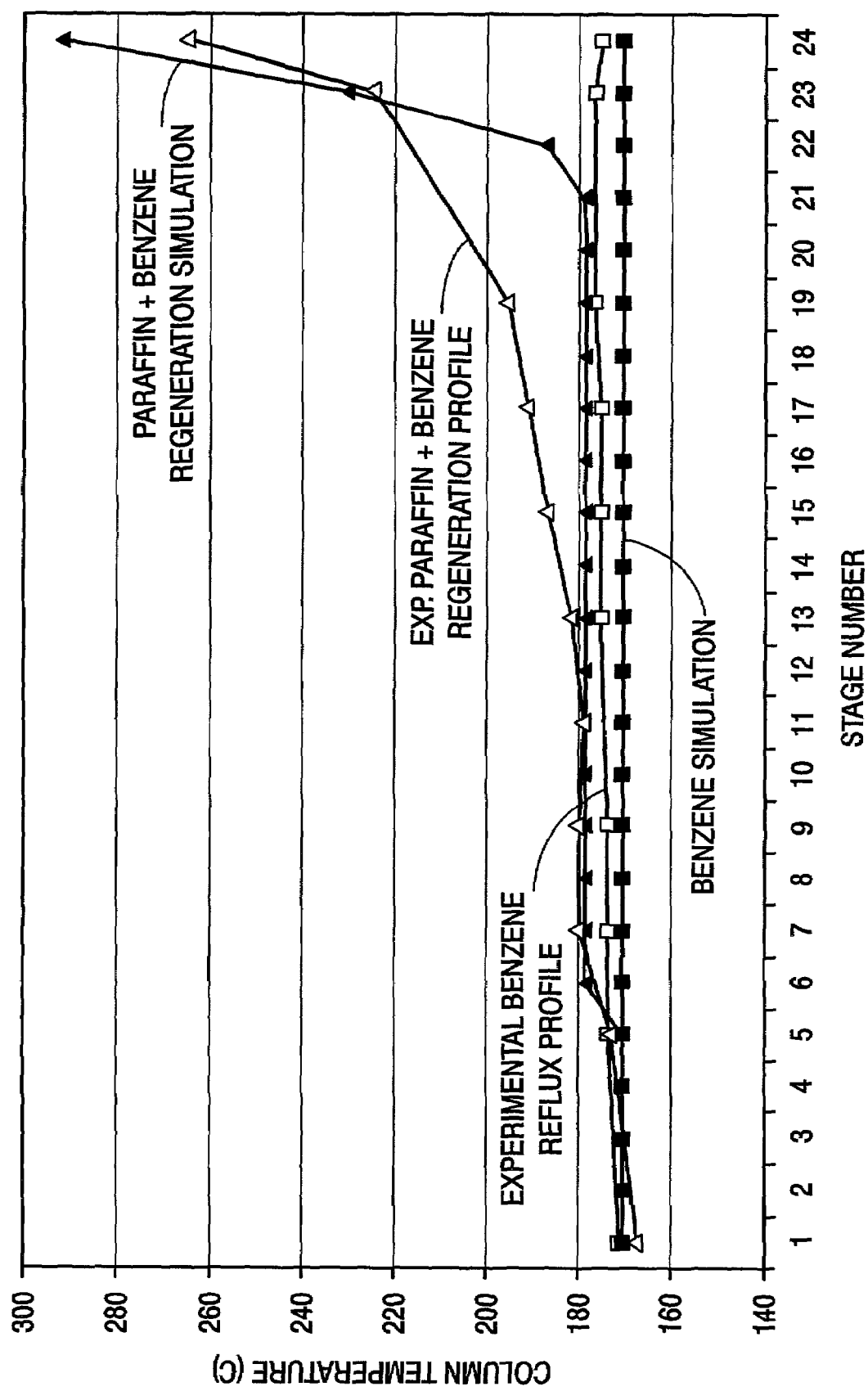
FIG. 3 is a graph comparing experimental data on paraffin plus benzene regeneration with simulated paraffin plus benzene regeneration.
Figure 4:
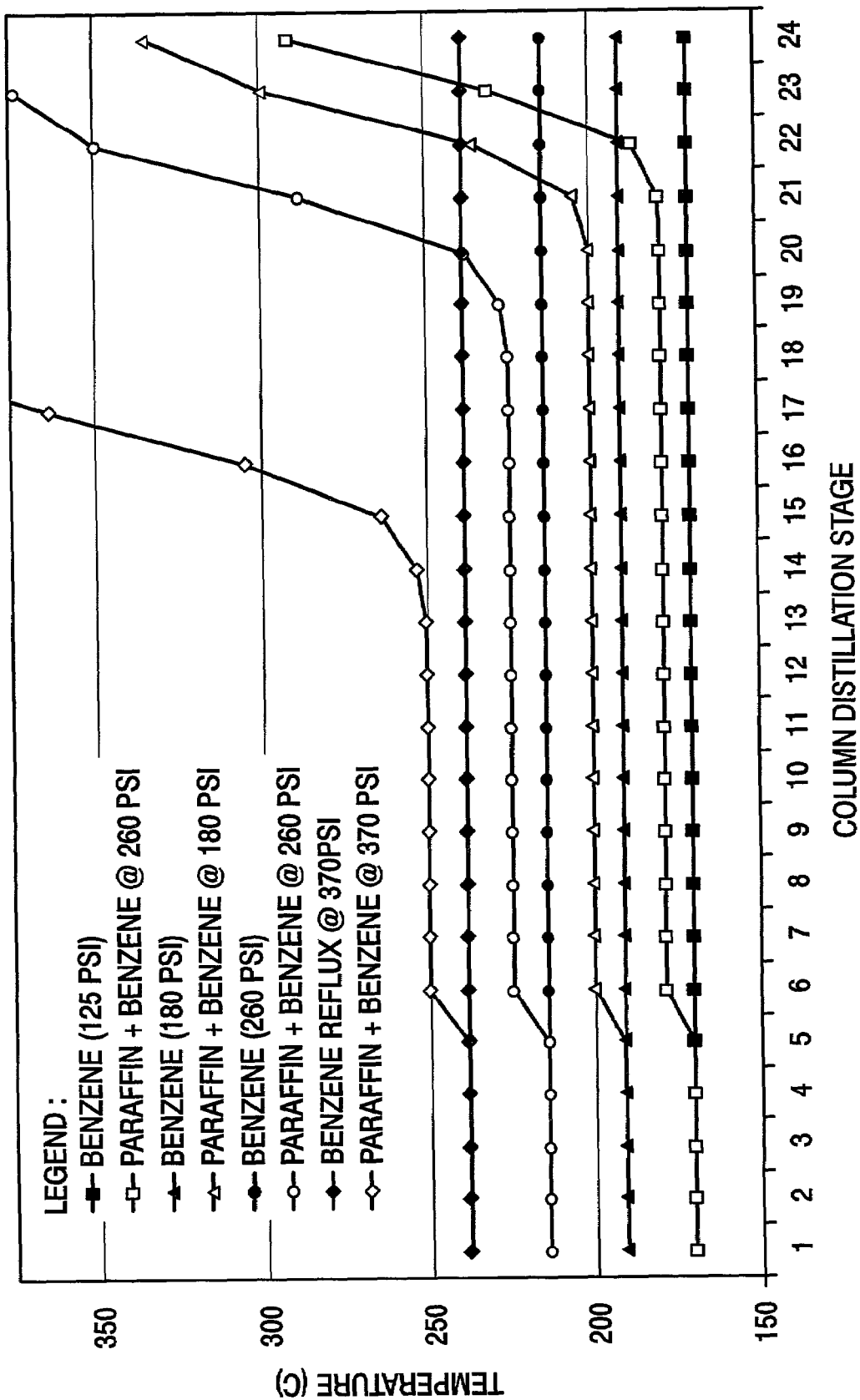
FIG. 4 is a graph similar to FIG. 3 showing simulated regenerations at higher pressures.

The injection of paraffin above the catalyst is one means of increasing the steady state regeneration temperature in the reactive distillation column. This paraffin injection provides a temperature increase as well as additional washing action to transport the by-products on the catalyst and transfers them to the reboiler. This effect of increased regeneration temperature with paraffin injection can be applied at higher pressure and will continue to achieve a stepwise advantage for reaching higher regeneration temperature at a given distillation column pressure. This effect can be modeled to determine the extent of the advantage beyond the pressure limit of the experimental reactive distillation column shown in FIG. 1. Table 3 and FIG. 3 compare experimental data at 125 psig, 50 g/min of $C_{10}$–$C_{13}$ paraffin injection above the catalyst bed, and 10 g/min. benzene injected below the bed at the base of section G with distillation, simulation using ASPEN Plus 10.1. The simulation conditions are identical to the experimental operating conditions with n-dodecane used to simulate the injected paraffin. The catalyst bed lies between Stage 6 and 18 for the simulation. The 125 psig pressure range is within the mechanical limit of the reactive distillation column shown in FIG. 1. FIG. 3 shows a good correlation between experimental data and the simulation. The advantage of counter-current paraffin injection and benzene at reflux can be shown by further simulations at higher column back pressures. These higher pressure simulations using ASPEN Plus 10.1, were all conducted at 50 g/min n-dodecane injection, 10 g/min benzene injection into Section G and at total benzene reflux. The data for the higher pressure simulations are shown in Table 4 and graphed in FIG. 4. The simulation at 180 psig shows that a regeneration temperature of 200° C. will be achieved. Increasing the pressure to 260 psig can achieve a regeneration temperature of 224° C. Increasing the column back pressure to 370° C. will achieve a regeneration temperature of 250° C. The simulations indicate that the combination of a counter-current paraffin injection with total benzene reflux will achieve increases in regeneration temperature of 8 to 12 degrees Centigrade while maintaining a uniform temperature in the catalyst zone placed between stages 6 and 18. The total benzene reflux also provides the maximum liquid phase benzene concentration in the catalyst zone. Commercial regeneration of fixed bed process requires 500 psig reactor pressures to maintain the benzene in the liquid phase inorder to achieve a 250° C. regeneration temperature.

TABLE 3

| Reactive Distillation Column Temperature Points | Simulation Stage Number | Benzene Simulation | Paraffin + Benzene Regeneration Simulation | Experimental Benzene Reflux Profile | Exp Paraffin + Benzene Regeneration Profile |
|---|---|---|---|---|---|
| Overhead Vapor Temp | 1 | 170.379 | 170.379 | 171.379 | 167.8276 |
|  | 2 | 170.379 | 170.379 |  |  |
|  | 3 | 170.379 | 170.380 |  |  |
|  | 4 | 170.379 | 170.387 |  |  |
| DA-220-1 | 5 | 170.380 | 170.634 | 173.439 | 173.3027 |
|  | 6 | 170.388 | 178.316 |  |  |
| DA-220-2 | 7 | 170.388 | 178.317 | 173.355 | 179.8502 |
|  | 8 | 170.388 | 178.317 |  |  |
| DA-220-3 | 9 | 170.388 | 178.317 | 173.138 | 180.136 |
|  | 10 | 170.388 | 178.317 |  |  |
| DA-220-4 | 11 | 170.388 | 178.317 | 170.337 | 178.9793 |
|  | 12 | 170.388 | 178.317 |  |  |

TABLE 3-continued

| Reactive Distillation Column Temperature Points | Simulation Stage Number | Benzene Simulation | Paraffin + Benzene Regeneration Simulation | Experimental Benzene Reflux Profile | Exp Paraffin + Benzene Regeneration Profile |
|---|---|---|---|---|---|
| TI-215 | 13 | 170.388 | 178.317 | 174.791 | 181.7515 |
|  | 14 | 170.388 | 178.317 |  |  |
| DA-210-1 | 15 | 170.388 | 178.317 | 174.700 | 187.0356 |
|  | 16 | 170.388 | 178.318 |  |  |
| DA-210-2 | 17 | 170.388 | 178.318 | 174.719 | 191.2626 |
|  | 18 | 170.388 | 178.318 |  |  |
| DA-210-3 | 19 | 170.388 | 178.320 | 176.403 | 195.5427 |
|  | 20 | 170.388 | 178.382 |  |  |
|  | 21 | 170.388 | 179.122 |  |  |
|  | 22 | 170.388 | 187.080 |  |  |
| DA-210-4 | 23 | 170.393 | 230.409 | 176.306 | 224.8719 |
| Reboiler Temp | 24 | 170.561 | 291.900 | 175.140 | 265.1487 |

TABLE 4

ASPEN Plus 10.1 Simulation of Effect of Paraffin Injection at the Top of the Catalyst Bed (above Stage 6) as a function of Column Back Pressure

| Column Distillation Stage | Benzene Reflux @ 125 psi | Paraffin + Benzene @ 125 psi | Temperature Increase In Catalyst (C.) | Benzene Reflux @ 180 psi | Paraffin + Benzene @ 180 psi | Temperature Increase In Catalyst (C.) | Benzene Reflux @ 260 psi | Paraffin + Benzene @ 260 psi | Temperature Increase In Catalyst (C.) | Benzene Reflux @ 370 psi | Paraffin + Benzene @ 370 psi | Temperature Increase In Catalyst (C.) |
|---|---|---|---|---|---|---|---|---|---|---|---|---|
| Top 1 | 170.38 | 170.38 | 0.00 | 191.01 | 191.19 | 0.18 | 214.27 | 214.28 | 0.00 | 238.57 | 238.57 | 0.00 |
| 2 | 170.38 | 170.38 | 0.00 | 191.01 | 191.19 | 0.18 | 214.27 | 214.28 | 0.00 | 238.57 | 238.57 | 0.00 |
| 3 | 170.38 | 170.38 | 0.00 | 191.01 | 191.19 | 0.18 | 214.27 | 214.28 | 0.00 | 238.57 | 238.57 | 0.00 |
| 4 | 170.38 | 170.39 | 0.01 | 191.01 | 191.20 | 0.19 | 214.27 | 214.30 | 0.02 | 238.57 | 238.61 | 0.04 |
| 5 | 170.38 | 170.63 | 0.25 | 191.01 | 191.54 | 0.52 | 214.27 | 214.79 | 0.51 | 238.57 | 239.34 | 0.77 |
| 6 | 170.38 | 178.32 | 7.93 | 191.01 | 199.90 | 8.89 | 214.27 | 224.34 | 10.07 | 238.57 | 250.32 | 11.76 |
| 7 | 170.38 | 178.32 | 7.93 | 191.01 | 199.90 | 8.89 | 214.28 | 224.34 | 10.07 | 238.57 | 250.32 | 11.76 |
| 8 | 170.38 | 178.32 | 7.93 | 191.01 | 199.90 | 8.89 | 214.28 | 224.34 | 10.07 | 238.57 | 250.32 | 11.76 |
| 9 | 170.38 | 178.32 | 7.93 | 191.01 | 199.90 | 8.89 | 214.28 | 224.34 | 10.07 | 238.57 | 250.32 | 11.76 |
| 10 | 170.38 | 178.32 | 7.93 | 191.01 | 199.90 | 8.89 | 214.28 | 224.34 | 10.07 | 238.57 | 250.33 | 11.76 |
| 11 | 170.38 | 178.32 | 7.93 | 191.01 | 199.90 | 8.89 | 214.28 | 224.34 | 10.07 | 238.57 | 250.34 | 11.77 |
| 12 | 170.38 | 178.32 | 7.93 | 191.01 | 199.90 | 8.89 | 214.28 | 224.34 | 10.07 | 238.57 | 250.42 | 11.85 |
| 13 | 170.38 | 178.32 | 7.93 | 191.01 | 199.90 | 8.89 | 214.28 | 224.34 | 10.07 | 238.57 | 250.85 | 12.28 |
| 14 | 170.38 | 178.32 | 7.93 | 191.01 | 199.90 | 8.89 | 214.28 | 224.34 | 10.07 | 238.57 | 253.09 | 14.52 |
| 15 | 170.38 | 178.32 | 7.93 | 191.01 | 199.90 | 8.89 | 214.28 | 224.34 | 10.07 | 238.57 | 263.78 | 25.21 |
| 16 | 170.38 | 178.32 | 7.93 | 191.01 | 199.90 | 8.89 | 214.28 | 224.35 | 10.07 | 238.57 | 304.99 | 66.42 |
| 17 | 170.38 | 178.32 | 7.93 | 191.01 | 199.90 | 8.89 | 214.28 | 224.39 | 10.12 | 238.57 | 364.42 | 125.86 |
| 18 | 170.38 | 178.32 | 7.93 | 191.01 | 199.91 | 8.89 | 214.28 | 224.70 | 10.43 | 238.57 | 410.14 | 171.57 |
| 19 | 170.38 | 178.32 | 7.94 | 191.01 | 199.92 | 8.91 | 214.28 | 226.83 | 12.56 | 238.57 | 446.67 | 208.11 |
| 20 | 170.38 | 178.38 | 8.00 | 191.01 | 200.05 | 9.04 | 214.28 | 239.46 | 25.19 | 238.57 | 466.16 | 227.59 |
| 21 | 170.38 | 179.12 | 8.74 | 191.01 | 204.99 | 13.97 | 214.28 | 288.01 | 73.73 | 238.56 | 477.54 | 238.97 |
| 22 | 170.38 | 187.08 | 16.70 | 191.01 | 235.15 | 44.14 | 214.28 | 350.28 | 136.01 | 238.56 | 482.38 | 243.82 |
| 23 | 170.38 | 230.41 | 60.03 | 191.01 | 299.93 | 108.91 | 214.28 | 373.54 | 159.26 | 238.56 | 484.47 | 245.91 |
| Reboiler 24 | 170.38 | 291.90 | 121.52 | 191.01 | 335.39 | 144.37 | 214.28 | 383.44 | 169.17 | 238.58 | 485.40 | 246.82 |

The data in Table 4 show that at high benzene reflux rates which achieve greater than 80 mole % benzene composition in the column, the paraffin injection provides an unexpected 7 to 15° C. temperature increase at all pressures from 125 psig to 370 psig. This confirms the experimental results of Example 2 as seen in Table 3.

EXAMPLE 3

Figure 5:
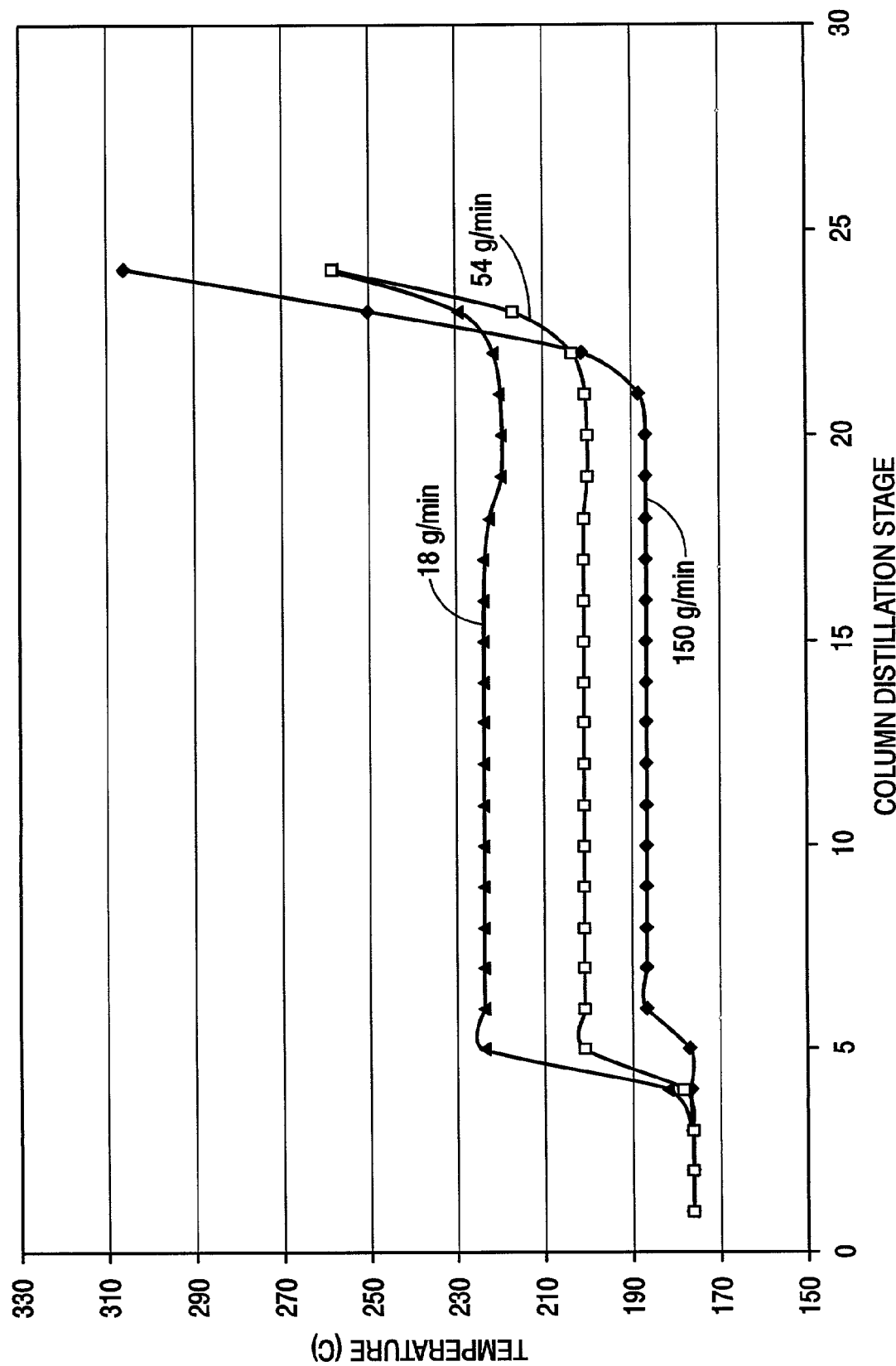
FIG. 5 is a graph showing regeneration temperatures as a function of benzene reflux rates.
Figure 6:
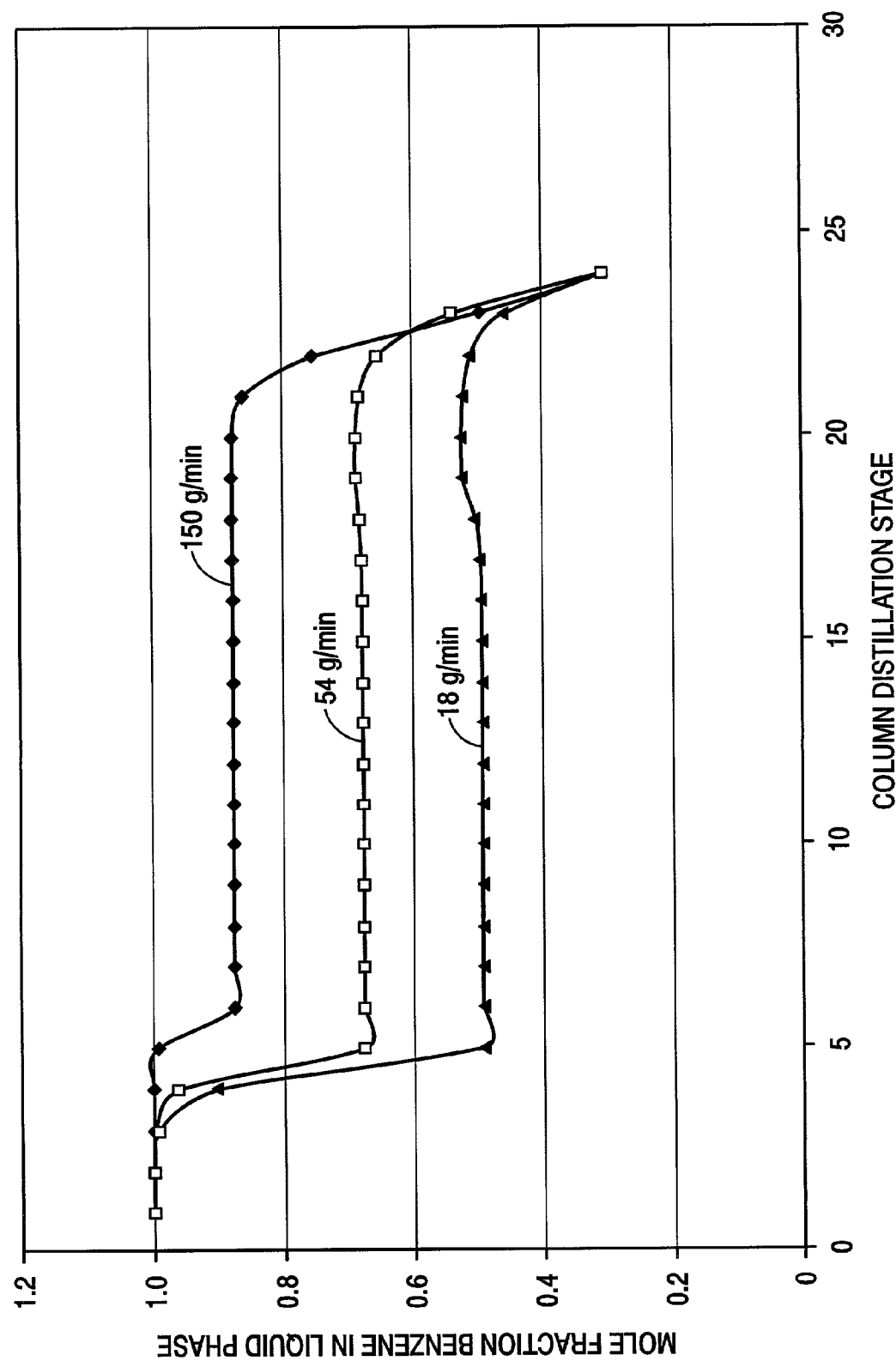
FIG. 6 is a graph showing the relationship between benzene reflux at various rates as a function of the mole % benzene.

Another mode of column operation can also be used to achieve high regeneration temperatures without significant increases in column pressure. This mode of operation also uses counter-current paraffin injection at the top of the catalyst bed and injection of benzene below the catalyst but maintained at reflux. A significant unexpected advantage from reducing the benzene reflux rate with paraffin injection was observed through ASPEN Simulation. Target regeneration temperatures in the range of 200° to 250° C. could be achieved by reducing the benzene reflux from 150 g/min down to 18 g/min while maintaining liquid phase benzene molar compositions of 50% to 87% in the catalyst zone. ASPEN Plus 10.1 using a RAD FRAC Model was used to determine the composition in the distillation column and the temperature in the catalyst zone. Simulation data is summarized in Table 5 and plotted in FIG. 5 and FIG. 6. The data shows that a steady state regeneration temperature of 200° C. within the catalyst bed (Stage 6 to Stage 18) can be achieved while maintaining a benzene liquid phase mole fraction of 67 mole %. This column composition and temperature is achieved at a reflux rate of 54 g/min of benzene at the top of the column. Similarly, a regeneration temperature of 223° C. is achieved with a further reduction of benzene reflux to 18 g/min while still maintaining a liquid phase molar benzene composition of 49 mole % in the catalyst zone. These compositions can be maintained for the 8 to 36 hours required to regenerate the catalyst.

TABLE 5

ASPEN Plus 10.1 RAD FRAC Simulation of Counter Current n-dodecane and Benzene Reflux at 125 psig, 50 g/min C12, 10 g/min Benzene

| Simulation Stage Number | Benzene Reflux Rate 150 g/min | | Benzene Reflux Rate 54 g/min | | Benzene Reflux Rate 18 g/min | |
|---|---|---|---|---|---|---|
| | Internal Temperature (C.) | Benzene Liquid Mole Fraction | Internal Temperature (C.) | Benzene Liquid Mole Fraction | Internal Temperature (C.) | Benzene Liquid Mole Fraction |
| 1 | 176.51 | 1.00000 | 176.04 | 0.99998 | 176.04 | 0.99994 |
| 2 | 176.51 | 1.00000 | 176.05 | 0.99974 | 176.08 | 0.99932 |
| 3 | 176.52 | 1.00000 | 176.23 | 0.99686 | 176.54 | 0.99193 |
| 4 | 176.53 | 0.99985 | 178.38 | 0.96204 | 182.08 | 0.90344 |
| 5 | 176.87 | 0.99461 | 200.69 | 0.67613 | 223.78 | 0.49149 |
| 6 | 186.55 | 0.87617 | 200.69 | 0.67613 | 223.78 | 0.49139 |
| 7 | 186.55 | 0.87618 | 200.69 | 0.67613 | 223.78 | 0.49139 |
| 8 | 186.55 | 0.87618 | 200.69 | 0.67613 | 223.78 | 0.49140 |
| 9 | 186.55 | 0.87617 | 200.69 | 0.67613 | 223.78 | 0.49141 |
| 10 | 186.55 | 0.87617 | 200.69 | 0.67615 | 223.77 | 0.49147 |
| 11 | 186.55 | 0.87617 | 200.68 | 0.67623 | 223.74 | 0.49164 |
| 12 | 186.55 | 0.87618 | 200.65 | 0.67657 | 223.66 | 0.49220 |
| 13 | 186.55 | 0.87618 | 200.62 | 0.67685 | 223.59 | 0.49264 |
| 14 | 186.55 | 0.87618 | 200.62 | 0.67686 | 223.58 | 0.49269 |
| 15 | 186.55 | 0.87618 | 200.62 | 0.67687 | 223.56 | 0.49286 |
| 16 | 186.55 | 0.87618 | 200.61 | 0.67694 | 223.48 | 0.49338 |
| 17 | 186.55 | 0.87618 | 200.58 | 0.67724 | 223.22 | 0.49510 |
| 18 | 186.55 | 0.87617 | 200.43 | 0.67865 | 222.36 | 0.50088 |
| 19 | 186.55 | 0.87616 | 199.78 | 0.68514 | 219.41 | 0.52122 |
| 20 | 186.72 | 0.87450 | 199.87 | 0.68420 | 219.46 | 0.52084 |
| 21 | 188.28 | 0.85885 | 200.40 | 0.67896 | 219.76 | 0.51876 |
| 22 | 201.14 | 0.75098 | 203.30 | 0.65123 | 221.34 | 0.50780 |
| 23 | 250.36 | 0.49332 | 217.20 | 0.53703 | 229.26 | 0.45651 |
| 24 | 306.20 | 0.30367 | 258.66 | 0.30356 | 258.66 | 0.30356 |

As seen in Table 5, at operating pressures as low as 125 psig and with sufficient paraffin injection, one can achieve a significant increase in column regeneration temperature by reducing the benzene reflux rate but still maintain significant and needed benzene concentration in the column. Thus, as seen from the data in Table 5, a reduction of the benzene concentration from 87 mole % to 50 mole % will shift the column regeneration temperature from about 186° C. to about 250° C.

As noted above, the counter-current paraffin injection permits a selection and tailoring of the regeneration conditions to suit a given catalyst. Some catalysts may require higher benzene concentrations at a given regeneration temperature. Those conditions can be achieved with paraffin injection and by adjusting the benzene reflux rate. Thus, one can achieve regeneration temperature at lower pressure and still maintain proper benzene composition.

Modifications of the apparatus, procedures and conditions disclosed herein that will still embody the concept of the improvements described should readily suggest themselves to those skilled in the art, and are intended to be encompassed within the spirit of the invention presently disclosed herein as well as the scope of the appended claims.

What is claimed is:

1. A process for the regeneration of a solid acid alkylation catalyst in a reactive distillation alkylation process taking place in a pressurized distillation column including an intermediate reactive catalyst zone having supported therein a solid acid alkylation catalyst, a first rectification zone at the top of the distillation column and a second rectification zone including a reboiler below said reactive catalyst zone, wherein at least a portion of an olefin-containing feedstock is brought into contact with at least a portion of an aromatic hydrocarbon feedstock in counter-current flow within the reactive catalyst zone, wherein the internal pressure in the reactive catalyst zone is maintained above 1 atmosphere and the temperature maintained at reflux of said aromatic hydrocarbon feedstock comprising:

A. periodically ceasing the introduction into the distillation column of the olefin-containing feedstock while continuing the flow of aromatic hydrocarbon feedstock and introducing into the column an effective amount of a paraffin feedstock at a point such that the paraffin feedstock intermixes in counter-current flow with the refluxing unreacted aromatic hydrocarbon feedstock as it flows through the catalyst to remove by-products from the catalyst;

B. adjusting the reflux rate of said aromatic hydrocarbon to achieve a desired temperature in the catalyst reaction zone above about 175° C. at a column operating pressure within the range of from about 125 to about 370 psig.

C. separating said by-products from said paraffin and aromatic hydrocarbon in said second rectification zone; and D. removing said by-products from said rectification zone.

2. The process of claim 1 where said second rectification zone includes a reboiler and said by-products are removed from said reboiler.

3. The process of claim 1 wherein the paraffin feedstock introduction is such that the mole percent of aromatic hydrocarbon in the catalyst zone is maintained at between about 40% to about 90%.

4. The process of claim 1 wherein the regeneration is carried out for a period of from about 8 to about 36 hours.

5. The process of claim 1 wherein said paraffin feedstock comprises $C_4$ to $C_{16}$ paraffin.

6. The process of claim 5 wherein said paraffin feedstock comprises $C_4$ to $C_{16}$ paraffins.

7. The process of claim 6 wherein said paraffin feedstock comprises $C_8$ to $C_{16}$ paraffins.

* * * * *